United States Patent [19]
Delmer et al.

[11] Patent Number: 6,166,301
[45] Date of Patent: Dec. 26, 2000

[54] METHOD FOR ASSAYING GENETIC ATTRIBUTES IN COTTON FIBER CELLS

[75] Inventors: Deborah P. Delmer; Doron Holland, both of Davis, Calif.

[73] Assignee: The Regents of the Unversity of California, Oakland, Calif.

[21] Appl. No.: 09/108,140

[22] Filed: Jun. 30, 1998

[51] Int. Cl.$^7$ .......................... C12N 15/82; C12N 15/84; C12N 5/04; C12N 15/29; A01H 4/00
[52] U.S. Cl. .......................... 800/314; 800/294; 800/278; 800/287; 435/427; 435/469; 536/23.6; 536/24.1
[58] Field of Search .............................. 435/172.3, 252.3, 435/410, 411, 419, 420, 469, 427; 800/294, 314, 278, 287; 536/23.6, 24.1

[56] References Cited

U.S. PATENT DOCUMENTS

| | | | |
|---|---|---|---|
| 5,004,863 | 4/1991 | Umbeck | 800/288 |
| 5,159,135 | 10/1992 | Umbeck | 800/314 |
| 5,602,321 | 2/1997 | Maliyakal | 800/314 |

FOREIGN PATENT DOCUMENTS

| | | |
|---|---|---|
| WO 92/15675 | 9/1992 | WIPO . |
| WO96/40924 | 12/1996 | WIPO . |

OTHER PUBLICATIONS

Shen, Wen–Hui, et al.: "T–DNA transfer to maize cells: Histochemical investigation of β–glucuronidase activity in maize tissues", *Proc. Natl. Acad. Sci USA*, 90:1488–1492 (1993).

John, Maliyakal E. "Cotton Crop Improvement Through Genetic Engineering", *Critical Reviews in Biotechnology*, 17(3):185–208 (1997).

Hansen, Genevieve, et al.: "Constitute expression of the virulence genes improves the efficiency of plant transformation by Agrobacterium", *Proc. Natl. Acad. Sci USA*, 91:7603–7607 (1994).

Umbeck et al. Biotechnology. 1987. vol. 5: 263–266.

*Primary Examiner*—David T. Fox
*Assistant Examiner*—Ousama Zaghmout
*Attorney, Agent, or Firm*—Townsend and Townsend and Crew LLP

[57] ABSTRACT

The present invention provides methods for testing gene expression in a cotton fiber cells. The methods comprise contacting the cell with Agrobacterium sp., comprising a recombinant T-DNA vector, which includes a plant promoter operably linked to a gene of interest; and detecting the product of the polynucleotide of interest, thereby testing for expression of the polynucleotide of interest.

13 Claims, No Drawings

METHOD FOR ASSAYING GENETIC ATTRIBUTES IN COTTON FIBER CELLS

FIELD OF THE INVENTION

The present invention is directed to plant genetic engineering. In particular, it relates to the transient expression of genes of interest in cotton fiber cells.

BACKGROUND OF THE INVENTION

A fundamental problem in genetic research involving cotton (Gossypium hirsutum) is the lack of a rapid and simple method to measure expression of a gene of interest in the cotton fiber cell. Evaluation of the phenotype of genes of interest is useful in designing transgenic plants with desired characteristics. Different genetic parameters may affect the phenotype produced by a gene of interest. For instance, various expression cassettes may regulate the expression of a gene of interest differently, thus changing the resulting phenotype of a transformed plant. One skilled in the art would recognize that an expression cassette may be altered so as to affect a corresponding phenotype. Such alterations include, inter alia: varying the type or length of the promoter and/or including or excluding enhancer elements, ribosomal binding sites, introns, and/or polyadenylation sites. Therefore, to obtain the optimal desired phenotype, transformation using many different variations of an expression cassette into the plant of interest is desirable.

Although methods for the transformation of cotton are known (Umbeck, U.S. Pat. Nos. 5,004,863 and 5,159,135; WO 92/15675, published Sep. 17, 1992), these methods typically have very low transformation efficiencies. Furthermore, these methods require a significant amount of time and greenhouse space to regenerate and identify transformed plants. Therefore much time and effort is expended to identify an expression cassette that produces the optimal desired phenotype.

Cotton is a plant of great commercial importance. One significant product from cotton plants, cotton fiber tissue, is used in the production of textiles. The cotton fiber cells that make up cotton fiber tissue are therefore of great interest. Manipulation of the cotton fiber cell phenotype can produce novel and economically important improvements to cotton fiber tissue and, thus, to textiles. Important qualities of the cotton fiber cell include, inter alia, fiber strength, length, color and debellatio.

Although transient expression has been documented in tobacco, maize and Arabidopsis, (see e.g., Hansen et al., Proc. Natl. Acad. Sci. USA 91: 7603–7607 (1994)), transient expression has never been achieved in such a specialized cell type as cotton tissue fiber cells. The invention presented herein addresses these and other problems.

SUMMARY OF THE INVENTION

The present invention provides methods for testing gene expression in a cotton fiber cells. The methods comprise contacting the cell with Agrobacterium sp., comprising a recombinant T-DNA vector, which includes a plant promoter operably linked to a polynucleotide of interest; and detecting the product of the polynucleotide of interest, thereby testing for expression of the polynucleotide of interest. Any of a number of promoters can be used in these constructs. Typically, a fiber-specific promoter, such as that from the Rac13 gene, is used. Other promoters such as, constitutive promoters can also be used. The age of the cotton fiber cell when it is contacted with the Agrobacterium is preferably between 9–14 days post-anthesis. Usually, Agrobacterium tumefaciens is used.

A number of desired polynucleotides can be used in the invention. For instance, genes which alter the color of the cotton fiber cell can be used. In such embodiments, the polynucleotide of interest may include sequences which target the product of the polynucleotide of interest to plastids in the cotton fiber cell. In other embodiments, the polynucleotide of interest is a reporter gene, such as β-glucuronidase. In these embodiments, the reported gene can be used to detect and measure expression of the vector. Thus, for instance, the ability of a promoter or other regulatory sequences to direct expression in cotton fiber cells can be tested.

The invention further provides cotton fiber cells comprising a recombinant T-DNA vector, which includes a plant promoter operably linked to a polynucleotide of interest as described above.

Definitions

The phrase "nucleic acid sequence" refers to a single or double-stranded polymer of deoxyribonucleotide or ribonucleotide bases read from the 5' to the 3' end. It includes chromosomal DNA, self-replicating plasmids, infectious polymers of DNA or RNA and DNA or RNA that performs a primarily structural role.

A "promoter" is defined as an array of nucleic acid control sequences that direct transcription of an operably linked nucleic acid. As used herein, a "plant promoter" is a promoter that functions in plants, even though obtained from other organisms, such as plant viruses. Promoters include necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The term "plant" includes whole plants, plant organs (e.g., leaves, stems, flowers, roots, etc.), seeds and plant cells and progeny of same. The class of plants which can be used in the method of the invention is generally as broad as the class of higher plants amenable to transformation techniques, including angiosperms (monocotyledonous and dicotyledonous plants), as well as gymnosperms. It includes plants of a variety of ploidy levels, including polyploid, diploid, haploid and hemizygous.

A polynucleotide sequence is "heterologous to" an organism or a second polynucleotide sequence if it originates from a foreign species, or, if from the same species, is modified from its original form. For example, a promoter operably linked to a heterologous coding sequence refers to a coding sequence from a species different from that from which the promoter was derived, or, if from the same species, a coding sequence which is different from any naturally occurring allelic variants.

A polynucleotide "exogenous to" an individual plant is a polynucleotide which is introduced into the plant by any means other than by a sexual cross. Examples of means by which this can be accomplished are described below, and include Agrobacterium-mediated transformation, biolistic methods, electroporation, and the like. Such a plant containing the exogenous nucleic acid is referred to here as an $R_1$ generation transgenic plant. Transgenic plants which arise from sexual cross or by selfing are descendants of such a plant.

A "polynucleotide of interest" is any polynucleotide whose expression can be detected in a plant cell, preferably a cotton fiber cell. The polynucleotide can encode a polypeptide of interest or transcribe a desired mRNA molecule, such as an antisense transcript. The polynucleotide of interest can also be a reporter gene used to test function of a promoter in cotton fiber cells. Examples of suitable reporter In the case of both expression of transgenes and inhibition of endogenous genes (e.g., by antisense, or sense suppression) one of skill will recognize that the inserted polynucleotide sequence need not be identical, but may be only "substantially identical" to a sequence of the gene from which it was derived.

In the case where the inserted polynucleotide sequence is transcribed and translated to produce a functional polypeptide, one of skill will recognize that because of codon degeneracy a number of polynucleotide sequences will encode the same polypeptide. Two nucleic acid sequences or polypeptides are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, *Computer Applic. Biol. Sci.* 4:11–17 (1988) e.g., as implemented in the program PC/GENE (Intelligenetics, Mountain View, Calif., USA).

A "recombinant T-DNA vector" refers to a polynucleotide sequence that contains at least one T-DNA border sequence and that is not integrated into plant chromosomal DNA.

The phrase "substantially identical," in the context of two nucleic acids or polypeptides, refers to sequences or subsequences that have at least 60%, preferably 80%, most preferably 90–95% nucleotide or amino acid residue identity when aligned for maximum correspondence over a comparison window as measured using one of the following sequence comparison algorithms or by manual alignment and visual inspection. This definition also refers to the complement of a test sequence, which has substantial sequence or subsequence complementarity when the test sequence has substantial identity to a reference sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, *J. Mol. Evol.* 35:351–360 (1987). The method used is similar to the method described by Higgins & Sharp, *CABIOS* 5:151–153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of algorithm that is suitable for determining percent sequence identity and sequence similarity is the BLAST algorithm, which is described in Altschul et al., *J. Mol. Biol.* 215:403–410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (1), Leucine (L), Methionine (M), Valine (V); and
6) Phenylalanine (F), Tyrosine (Y), Tryptophan (W).
(see, e.g., Creighton, Proteins (1984)).

An indication that two nucleic acid sequences or polypeptides are substantially identical is that the polypeptide encoded by the first nucleic acid is immunologically cross reactive with the antibodies raised against the polypeptide encoded by the second nucleic acid. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes,* "Overview of principles of hybridization and the strategy of nucleic acid assays" (1993). Generally, highly stringent conditions are selected to be about 5–10° C. lower than the thermal melting point ($T_m$) for the specific sequence at a defined ionic strength pH. Low stringency conditions are generally selected to be about 15–30° C. below the $T_m$. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 time background hybridization.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cased, the nucleic acids typically hybridize under moderately stringent hybridization conditions.

In the present invention, genomic DNA or cDNA comprising nucleic acids of the invention can be identified in standard Southern blots under stringent conditions using the nucleic acid sequences disclosed here. For the purposes of this disclosure, suitable stringent conditions for such hybridizations are those which include a hybridization in a buffer of 40% formamide, 1 M NaCl, 1% SDS at 37° C., and at least one wash in 0.2×SSC at a temperature of at least about 50° C., usually about 55° C. to about 60° C., for 20 minutes, or equivalent conditions. A positive hybridization is at least twice background. Those of ordinary skill will readily recognize that alternative hybridization and wash conditions can be utilized to provide conditions of similar stringency.

A further indication that two polynucleotides are substantially identical is if the reference sequence, amplified by a pair of oligonucleotide primers, can then be used as a probe under stringent hybridization conditions to isolate the test sequence from a cDNA or genomic library, or to identify the test sequence in, e.g., a northern or Southern blot.

DETAILED DESCRIPTION OF THE INVENTION

This invention provides methods for assaying the phenotype of a gene of interest in a cotton fiber cell without regenerating whole transgenic plants. This invention also provides a method for measuring the activity of a promoter of interest in a cotton fiber cell without regenerating whole transgenic plants.

I. Preparation of recombinant vectors

Generally, the nomenclature and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook et al., *Molecular Cloning—A Laboratory Manual,* Cold Spring Harbor Laboratory, Cold Spring Harbor, N.Y., (1989).

A. Promoters

To perform the invention, recombinant DNA vectors suitable for transformation of plant cells are prepared. The DNA vector may include a polynucleotide of interest coding for a desired polypeptide. For example, a cDNA sequence encoding a full length protein, is conveniently combined with transcriptional and translational initiation regulatory sequences which will direct the transcription of the sequence from the gene in a cotton fiber cell.

Various transcriptional regulatory sequences are known. For example, for overexpression, a plant promoter fragment may be employed which will direct expression of the gene of interest. Such promoters are referred to herein as "constitutive" promoters and are active under most environmental conditions and states of development or cell differentiation. Examples of constitutive promoters include the cauliflower mosaic virus (CaMV) 35S transcription initiation region, the 1′- or 2′- promoter derived from the T-DNA of *Agrobacterium tumafaciens,* various ubiquitin or polyubiquitin promoters derived from, inter alia, Arabidopsis (Sun and Callis, *Plant J.,* 11(5):1017–1027 (1997)), the mas, Mac or DoubleMac promoters (described in U.S. Pat. No. 5,106,739 and by Comai et al., *Plant Mol. Biol.* 15:373–381 (1990)) and other transcription initiation regions from various plant genes known to those of skill in the art. Such genes include for example, ACT11 from Arabidopsis (Huang et al., *Plant Mol. Biol.* 33:125–139 (1996)), Cat3 from Arabidopsis (GenBank No. U43147, Zhong et al., *Mol. Gen. Genet.* 251:196–203 (1996)), the gene encoding stearoyl-acyl carrier protein desaturase from *Brassica napus* (Genbank No. X74782, Solocombe et al., *Plant Physiol.* 104:1167–1176 (1994)), GPc1 from maize (GenBank No. X15596, Martinez et al., *J. Mol. Biol* 208:551–565 (1989)), and Gpc2 from maize (GenBank No. U45855, Manjunath et al., *Plant Mol. Biol.* 33:97–112 (1997)).

Alternatively, the plant promoter may direct expression of the gene of interest in a specific tissue such as the cotton fiber cell and/or associated ovules under more precise environmental or developmental control. Examples of environmental conditions that may effect transcription by inducible promoters include anaerobic conditions, elevated temperature, or the presence of light. Such promoters are referred to here as "inducible" or "tissue-specific" promoters. One of skill will recognize that a tissue-specific promoter may drive expression of operably linked sequences in tissues other than the target tissue. Thus, as used herein a tissue-specific promoter is one that drives expression preferentially in the target tissue, but may also lead to some expression in other tissues as well.

Examples of promoters under developmental control include promoters that initiate transcription only (or primarily only) in certain tissues, such as cotton fiber, seed, or flowers. Promoters that direct expression of nucleic acids in cotton fibers and ovules are particularly useful in the present invention. As used herein a cotton fiber-specific promoter is one which directs expression in cotton fiber cells. Examples include a promoter from the cotton fiber-specific Rac13 gene described in pending PCT application No. WO 96/40924 (published Dec. 19, 1996) and Delmer et al, *Mol. Gen. Genet.* 248:43–51 (1994). Other suitable cotton-fiber specific promoters are derived from the following: the 4—4 cDNA clone and the lipid transfer protein (both described in PCT WO 96/40924 (Dec. 19, 1996)) and the E6 cDNA (described in John and Crow, *Proc. Natl. Acad. Sci. USA,* 89(13):5769–5773 (1992).

Methods for isolation of promoters are known. For instance, the full length of a promoter sequence may be isolated if a portion of the promoter or the corresponding gene sequence is known. One skilled in the art will recognize that a variety of small or large insert genomic DNA libraries may be screened using hybridization or polymerase chain reaction (PCR) technology to identify library clones containing the desired sequence. Typically, the desired sequence may be used as a hybridization probe to identify individual library clones containing the known sequence. Alternatively, PCR primers based on the known sequence may be designed and used in conjunction with other primers to amplify sequences adjacent to the known DNA polynucleotide sequence. Library clones containing adjacent DNA sequences may thereby be identified. Restriction mapping and hybridization analysis of the resulting library clones' DNA inserts allows for identification of the DNA sequences adjacent to the known DNA polynucleotide sequence. Thus, promoters may be isolated if only a portion of a promoter sequence is known.

If proper polypeptide expression is desired, a polyadenylation region at the 3′-end of the coding region should be included. The polyadenylation region can be derived from the natural gene, from a variety of other plant genes, or from a T-DNA.

As used herein, gene expression may result from transient or stable expression of a polynuleotide sequence in a plant cell. Transient expression detected in the methods of the invention refers to introduction and detection of a polynucleotide in a cell that is not integrated into the cell's chromosomes. Stable expression includes introduction of a DNA polynucleotide sequence into a cell's chromosomes. Either mechanism of expression (i.e. transient or stable) may be used in the present invention.

B. Polynucleotides of Interest

This invention provides, inter alia, for a method to express genes of interest in a cotton fiber cell. Of particular interest are genes the affect qualities of the cotton fiber cell such as fiber strength, length, color, texture and debellatio. See generally, pending PCT application No. WO 96/40924 published Dec. 19, 1996. Multiple polynucleotide sequences may be expressed simultaneously by the methods of this invention. If multiple polynucleotide sequences are expressed, the polynucleotide sequences may either function to express the same or different phenotypes.

Among the genes that affect cotton fiber color are genes involved in the production of melanin and indigo. Melanins are dark brown pigments found in plants, animals and microorganisms. Examples of genes affecting melanin production include the tyrosinase gene and ORF438 from *Streptomyces antibioticus*. Indigo production is affected by monooxygenases such as xylene oxygenase which oxidizes toluene and xylene to (methyl) benzyl alcohol and also transforms indole into indigo. Other genes such as naphthalene dioxygenase and tryptophanase also affect indigo production.

Typically, the products of such genes are targeted for expression in organelles in the fiber cell, particularly plastids. Plastid targeting sequences are known from a number of nuclear genes encoding plastid proteins. Examples of suitable targeting sequences are provided in WO 96/40924, supra.

Reporter genes may also be expressed from an expression cassette 15 according the method of this invention. Reporter genes are often used to indirectly measure the rate of transcription from a promoter. A commonly used reporter gene in plants encodes β-glucuronidase (GUS). After cells are transformed with an expression cassette including a promoter operably linked to the GUS gene, GUS enzyme activity may be measured using X-Glc as a substrate (Jefferson, *EMBO J.*, 6:3901–3907 (1987)). The GUS enzyme converts the substrate into a blue chemical which may be quantified using photospectrometry as will be recognized by one skilled in the art. Other reporter genes include, inter alia: β-galactosidase and green fluorescent protein.

Expression products of expressed genes can be detected in many ways, depending on the nature of the product. Detection methods include immuno-assays, enzyme assays or visual inspection. For example, methods of detecting expression of reporter genes such as GUS are disclosed below. The assays are typically carried out less than 72 hours after contact with the Agrobacterium. Preferably, assays are carried out from 6 to 60 hours after contact. More preferably, the assays are carried out from 12 to 48 hours after contact.

II. Transformation of DNA constructs into cotton fiber cells

DNA constructs of the invention may be introduced into cotton fiber cells by a variety of conventional techniques. A key difference between these transformation techniques and the invention at issue is that in the invention at issue, no plants are regenerated and no selection of transformed plants (e.g. using an antibiotic such as kanamycin to select against untransformed plants) is necessary. DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. *Agrobacterium tumefaciens*-mediated transformation techniques, including disarming and use of binary vectors, are well described in the scientific literature. See, for example Horsch et al,. *Science* 233:496–498 (1984), and Fraley et al., *Proc. Natl. Acad. Sci. USA* 80:4803 (1983).

The DNA construct also may be introduced directly into the plant cell using techniques such as electroporation and microinjection of plant cell protoplasts, or the DNA constructs can be introduced directly to plant tissue using ballistic methods, such as DNA particle bombardment. Microinjection techniques are known in the art and well described in the scientific and patent literature. The introduction of DNA constructs using polyethylene glycol precipitation is described in Paszkowski et al., *EMBO J.* 3:2717–2722 (1984). Electroporation techniques are described in Fromm et al., *Proc. Natl. Acad. Sci. USA* 82:5824 (1985). Ballistic transformation techniques are described in Klein et al., *Nature* 327:70–73 (1987).

The age of the ovules which bear the cotton fiber cells used in the methods of the invention can be selected to provide expression of the introduced construct. In particular, the age of the ovule is preferably between about 7 and about 15 days post-anthesis. A more preferred range is between about 9 and about 14 days.

The following Example is offered by way of illustration, not limitation.

EXAMPLE 1

Cotton fibers that were 9 to 14 days post-anthesis were cultured in vitro with their associated ovules according to the method of Beasley and Ting, *Amer. J. Bot.* 60:130–139 (1973). Engineered *Agrobacterium tumefaciens* EHA105 (see Hood et al.,*J. Bacteriol.* 168:1283–1290 (1986)) grown to mid-log phase and harboring binary vector pBI101.1 (for sequence and technical data, see http://vectordb.atcg.com/vectordb/ vector_descrip/COMPLETE/PBI101.SEQ.html) that contained the β-glucuronidase (GUS) reporter gene operably linked to the Rac13 promoter (see PCT WO 96/40924 (Dec. 19, 1996)) was subsequently contacted to the cotton ovules/fibers for one hour. The ovules/fibers were then rinsed and then co-cultivated for two days at 30° C. The bacteria were subsequently removed by two successive washes of the ovules/fibers with growth medium containing 70 μg/mL carbenicillin. The ovules/fibers were then incubated for 24 hours at 30° C.

Fibers were assayed for GUS expression by assaying for GUS enzyme activity using X-Glc as a substrate. Strong expression of the GUS reporter gene was observed within minutes from the beginning of the assay, indicating high levels of transient expression. Microscopic examination revealed that the enzyme activity resided within the cotton fiber cells and that at least 50% of the total fibers expressed GUS activity. *Agrobacterium tumefaciens* cells containing the expression cassette did not express GUS activity. In experiments where the RAC13 promoter was replaced with the 1', 2' promoter from *A. tumefaciens*, the cotton fibers had detectable, but weaker expression compared to the Rac13 construct.

The above example is provided to illustrate the invention but not to limit its scope. Other variants of the invention will be readily apparent to one of ordinary skill in the art and are encompassed by the appended claims. All publications, patents, and patent applications cited herein are hereby incorporated by reference.

What is claimed is:

1. A method for testing gene expression in a cotton fiber cell without regenerating a whole transgenic plant, the method comprising:

contacting an isolated cotton fiber cell, which is attached to an ovule, with Agrobacterium sp., said Agrobacterium sp. comprising a recombinant T-DNA vector, which vector comprises a plant promoter operably linked to a polynucleotide of interest; and detecting the product of the polynucleotide of interest, thereby testing for expression of the polynucleotide of interest under the control of said promoter in the isolated cotton fiber cell.

2. The method of claim 1, wherein the promoter is a fiber-specific promoter.

3. The method of claim 2, wherein the fiber-specific promoter is a Rac13 promoter.

4. The method of claim 1, wherein the promoter is a constitutive promoter.

5. The method of claim 1, wherein the cotton fiber cell is contacted with the Agrobacterium between about 9 and about 14 days post-anthesis.

6. The method of claim 1, wherein the Agrobacterium is *Agrobacterium tumefaciens*.

7. The method of claim 1, wherein the polynucleotide of interest alters the color of the cotton fiber cell.

8. The method of claim 7, wherein the polynucleotide of interest includes sequences which target the product of the polynucleotide of interest to plastids in the cotton fiber cell.

9. The method of claim 1, wherein the polynucleotide of interest is a reporter gene.

10. The method of claim 9, wherein the reporter gene encodes β-glucuronidase.

11. The method of claim 1, wherein the cotton fiber cell is co-cultivated with the Agrobacterium sp. for up to 72 hours.

12. The method of claim 11, wherein the cotton fiber cell is co-cultivated with the Agrobacterium sp. from 6 to 60 hours.

13. The method of claim 12, wherein the cotton fiber cell is co-cultivated with the Agrobacterium sp. from 12 to 48 hours.

* * * * *